United States Patent [19]

Lentsch

[11] 4,199,602

[45] Apr. 22, 1980

[54] CONTROL OF MASTITIS AND COMPOSITIONS THEREFOR

[75] Inventor: Steven E. Lentsch, St. Paul, Minn.

[73] Assignee: Economics Laboratory, Inc., St. Paul, Minn.

[21] Appl. No.: 970,653

[22] Filed: Dec. 18, 1978

Related U.S. Application Data

[63] Continuation-in-part of Ser. No. 880,335, Feb. 23, 1978, abandoned.

[51] Int. Cl.$^2$ .................. A61K 31/045; A61K 31/195
[52] U.S. Cl. ..................................... 424/343; 424/319
[58] Field of Search .............................. 424/319, 343

[56] References Cited

U.S. PATENT DOCUMENTS

| | | | |
|---|---|---|---|
| 2,806,789 | 9/1957 | Kiser et al. | 424/227 |
| 2,904,468 | 9/1959 | Davis et al. | 424/315 |
| 3,558,788 | 1/1971 | Clark et al. | 424/343 |
| 3,629,464 | 12/1971 | Nosler et al. | 424/334 |

OTHER PUBLICATIONS

Noesler et al.–Chem. Abst. vol. 71 (1969) p. 49,242k.
Hague et al.–Antimicrobial Agents & Chemotherapy, vol. 6 (Aug. 1974) p. 200.

*Primary Examiner*—V. D. Turner
*Attorney, Agent, or Firm*—Merchant, Gould, Smith, Edell, Welter & Schmidt

[57] ABSTRACT

Neutral to mildly acidic externally-applied mastitis control agents based upon antimicrobial nitroalkanols (e.g. 2-bromo-2-nitropropane-1,3-diol) can be made more effective against *Pseudomonas aeruginosa* through "potentiation" with an aminocarboxylic-type chelating agent. The chelating agent is believed to improve cell-wall permeability, even at a pH well below 7.

20 Claims, No Drawings

CONTROL OF MASTITIS AND COMPOSITIONS THEREFOR

This application is a continuation-in-part of my copending application, U.S. Ser. No. 880,335, filed Feb. 23, 1978, now abandoned.

BACKGROUND OF THE INVENTION

Milking of cows on a large scale is almost entirely done with a milking machine. The milking machine draws the milk from the cow's udder by pulsating vacuum, e.g. by attaching a teat cup connected to a vacuum pump and pulsating the vacuum to alternately allow the milk to fill and drain from the area of the udder and test to simulate hand milking of the cow. The tendency is to minimize the milking time by using high vacuum which causes irritation to the teat and udder.

The milk secreted through the teat canal is essentially sterile. However, contamination of the test environment is virtually unavoidable under normal field conditions, even when sterilized milking equipment is used. A wide variety of microorganisms can be present on or near the cow's udder and may even enter the teat canal, thus creating the possibility of infection.

The damage to tissue caused by the milking machine followed by exposure of the damaged tissue to certain microorganisms can result in an infection known as mastitis. This problem is of great economic importance to the dairy farmers because the infected cow's contaminated milk cannot be marketed. The infected udder must be treated with an antibiotic. However, the milk from such cows cannot be sold until the antibiotic is absent from the milk (usually about 3–5 days after the last treatment with the antibiotic).

According to experts, the dipping of tests in an antimicrobial (biostatic or biocidal) solution after milking is one of the most effective procedures that a dairy farmer can follow to prevent infections of the udder. An essential purpose of the teat dip is to prevent mastitis by killing or controlling the microorganisms and by helping heal any injured tissue. The teat dip product desirably has a wide spectrum of antibacterial activity to minimize infection, typically has emollient properties to promote healing and typically is or can be buffered to approximate "skin" pH, thereby minimizing irritation possibilities.

Prior Art

A number of teat dip products or mastitis control agents are available to dairy farmers which have varying degrees of effectiveness. These products or agents have in common an antimicrobial or sanitizing agent which is an active ingredient (usually the principal active ingredient) of the treating solution.

The following references are believed to be illustrative of published scientific and patent literature regarding teat dips:
  British Pat. No. 1,144,637 (Kilco Chemicals Ltd.), published Mar. 5, 1969
  U.S. Pat. No. 3,993,777, issued Nov. 23, 1976
  U.S. Pat. No. 4,025,628, issued May 24, 1977
  "Modern Teat Dips," appearing in The Veterinary Record, Vol. 93 (No. 133), Dec. 15, 1973
  Philpot et al, J. Dairy Science, 58(a):209

As will be apparent from these references, numerous antimicrobial agents have been investigated, including iodphors, PVP-iodine (a particular iodophor), hypochlorites, chlorine dioxide, chlorinated isocyanurates (chlorinated-S-triazene-trione), bromine, hydroxyquinone, ammonium chloride, chlorhexidine, hexachlorophene, diaphene, cetyl pyridinium chloride, and the quaternary ammonium germicides disclosed in the aforementioned U.S. Patent 3,993,777. Of the topically applied agents which have been investigated for control of bovine mastitis, iodophors, quaternary ammonium compounds, and chlorine-releasing sanitizing agents (particularly sodium hypochlorite and, more recently, chlorinated isocyanurates) presently appear to have gained the widest acceptance among dairy farmers, despite the fact that some of the chlorine-releasing sanitizers (e.g. 4% aqueous NaOCl) can have an irritating effect upon cow teats. (The irritation can be mitigated with emollients but may still occur.) And, at this stage of commercial development of the iodophors, there is some concern on the part of researchers who believe that this sanitizing agent may be capable of contaminating the milk. Teat dips of the future may have to be iodine-free.

An iodine-free teat dip which appeared in the marketplace fairly recently is sold by the Babson Brothers Company of Oakbrook, Illinois, U.S.A. under the trademark "SURGE". According to the "SURGE" label, this teat dip contains lauryl-poly-1-oxypropene, ethoxylated sterols and ethoxylated lipids, propylene glycol, and, presumably as its principal active ingredient, the antimicrobial agent 2-bromo-2-nitropropane-1,3-diol. The principal inactive ingredients in "SURGE" are water and a colorant (F, D and C No. 6). Experiments with the "SURGE" formula appear to indicate that this formula is less effective than the commercially available iodophors, however.

The patent literature contains an extensive discussion of the antimicrobial properties of nitroalkanols such as 2-bromo-2-nitropropane-1,3-diol and its analogs; see U.S. Pat. No. 3,558,788 (Clark et al), assigned to Boots Pure Drug Company Limited of Notthingham, England. This patent describes a method of combatting aerobic pathogenic bacteria on the surface of the skin by applying an antibacterially effective amount of a suitable nitroalkanol in a pharmaceutically acceptable carrier. Clark et al also discuss the spectrum of activity of these nitroalkanols, including their effectiveness against gram negative organisms such as *Pseudomonas pyocyanea* which have hitherto proved to be extremely resistant to known antibacterial agents. This patent reference further gives data in Table 2, column 5, where the minimum inhibitory concentration of 2-bromo-2-nitropropane-1,3-diol is given. The data reportedly is based on a test wherein appropriate solutions of the antibacterial agent in water or acetone were diluted with melted nutrient agar, mixed and allowed to solidify. The surface of the agar was inoculated with an appropriate bacterial suspension and incubated at 37° C. and observed for growth-after 18 hours of incubation. This test, while valid for determining inhibitory concentrations of antibacterial substances, does not indicate whether the organisms are killed or merely prevented from multiplying. For many uses such as preserving of pharmaceuticals, shampoos, etc. this test is believed to be a perfectly valid method of screening antimicrobial agents. However, a minimum inhibitory concentration is generally much lower than a killing concentration. Often there is a lack of correlation between the two figures in comparing different antimicrobial agents. That is, two antibacterial substances which have approximately the same minimum inhibitory concentration may differ widely in their killing concentration. Thus, depending on the intended use and purposes, both the minimum inhibitory concentration and the killing concentration must be determined to give a guide to a meaningful use-concentration. In a topical application such as a teat dip product (as against intramuscular injection), killing the organism is much more effective in preventing infection than merely inhibiting the organism.

The owners of the Clark et al patent have described the antibacterial characteristics of 2-bromo-2-nitropropane-1,3-diol in a technical bulletin entitled "Bronopol" published by the patent owners. On pages 11 and 12 of that technical bulletin, the patent owners describe the bactericidal activity of "Bronopol". Specifically, the patent owners found that "Bronopol" is bactericidal in 24 hours at 37° C. at concentrations only slightly higher (2-4 fold) than bacteriostatic levels. In tests to determine the bactericidal activity over short time periods, the patent owners found that "Bronopol" was more active against gram-negative than against gram-positive bacteria. The bactericidal effect of aqueous solutions of "Bronopol" at 22° C. and 37° C. against three species of bacteria was conducted by inoculation of 1 ml of aqueous suspensions of the various test organisms containing approximately $1 \times 10^6$ organisms/ml with 9 ml amounts of aqueous solutions of "Bronopol". Counts were made at various intervals by diluting 1 ml amounts of the "Bronopol" solution into peptone water and plating 1 ml amounts of these dilutions in nutrient agar without an inactivating agent. The results of those tests can be found in Table 5 on page 12 of the technical bulletin. The patent owners found that the bactericidal activity of freshly prepared solutions of "Bronopol" showed little variation over a pH range of 5-8 and was not greatly reduced in the presence of 50% serum.

It is known in the art that linear alkylbenzene sulfonates or linear alkylbenzene sulfonic acids are moderately effective bactericides, particularly in acid mediums. However, they are generally more active against a gram positive organism such as *Staphylococcus aureus* than against a gram negative organism. Also, a high level of a linear alkylbenzene sulfonate is undesirable for use in a teat dip product because it may defat the tissue and promote skin irritation.

The effect of chelating agents such as ethylene diamine tetra-acetic acid (EDTA), on certain gram negative bacteria, including *Pseudomonas aeruginosa*, has been studied. (*Pseudomonas aeruginosa* is synonymous with *Pseudomonas pyocyanea* according to *Bergey's Manual of Determinative Bacteriology*, Eighth Ed., The Williams and Wilkins Company, Baltimore, Md., pp. 221-222.) For example, in an article entitled "The Effect of Ethylene-diaminetetra-acetic Acid on the Cell Walls of Some Gram-Negative Bacteria" by G. W. Gray and S. G. Wilkinson, published in *The Journal of General Microbiology*, Volume 39, p. 385 (1965), the authors disclose that EDTA had a lytic bactericidal action on *Pseudomonas aeruginosa*. By treating the cell walls of *Pseudomonas aeruginosa* with a 0.003 M solution of EDTA and a borate buffer of pH 9.2 for one hour at 18°-20° C., the authors found that the turbidity of the aqueous suspensions of the walls was substantially decreased (about 30%). (See pages 386 and 394.) In an article entitled "Effect of Ethylenediaminetetra-acetic Acid and Related Chelating Agents on Whole Cells of Gram-Negative Bacteria" by H. Haque and A. D. Russell published in *Antimicrobial Agents and Chemotherapy*, Vol. 5, No. 5, pp. 447-452, May 1974, the authors found that EDTA dissolved in a borate buffer of pH 7.8 or 9.2 was fairly effective in reducing the viability of two strains of *Pseudomonas aeruginosa* when treated for fairly long periods of time, i.e. 30-60 minutes. The authors also noted that the bactericidal effect of EDTA was greater at pH 9.2 than at pH 7.8. (See pages 447-449.)

The effect of chelating agents such as EDTA (and various other aminocarboxylic-type chelating agents) on the susceptibility of certain strains of gram negative bacteria to certain antibacterial agents has also been studied. In an article entitled "Effective Chelating Agents" written by H. Haque and A. D. Russell published in *Antimicrobial Agents and Chemotherapy*, Vol. 6, page 200 (August 1974), the authors disclose that pretreatment with a chelating agent such as EDTA increased the susceptibility of two strains of *Pseudomonas aeruginosa* to the antibacterial action of cetrimide, clorhexidine, and benzalkonum chloride when treated for relatively long periods of time, i.e. 30-60 minutes. Besides EDTA, the other aminocarboxylic-type chelating agents studied by the authors were cyclohexane-1,2-diaminetetraacetic acid (CDTA), N-hydroxyethylethylenediaminetriacetic acid (HEDTA), iminodiacetic acid (IDA), and nitriloacetic acid (NTA, sometimes called nitrilotriacetic acid). The authors also disclose that pretreatment with EDTA increased the susceptibility of the foregoing two strains to $\beta$-lactam antibiotics, in partiuclar carbenicillin, but not as much as with respect to the other antibacterial agents when exposed for relatively long periods of time, i.e. 30-60 minutes. In order to carry out the pretreatment process, the authors suspended the particular strain of bacteria in a "Tris" buffer of pH 7.8 ("Tris" is tris[hydroxymethyl-]aminomethane) added to a Tris-buffered solution of EDTA having a pH of 9. The authors then added the EDTA solution with bacteria to a solution of a particular antibacterial agent or antibiotic previously equilibrated at 37° C. After addition to the antibacterial or antibiotic solution, the mixture was incubated at 37° C. Samples were removed immediately and at 30, 45 and 60 minutes for determination of the number of viable cells per milliliter or in the case of the antibiotic; immediately and at 30 and 60 minutes.

In the control of bovine mastitis, rapid killing of bacteria is essential, since prolonged treatment (e.g. more than 15 minutes or even more than a minute) with the teat dip is normally impractical. Bactericidal tests of teat dip formulas should be conducted with a view toward measuring the short-term kill. Perhaps more important, field studies and field experience with known bactericidal teat dip compositions tend to indicate that in vitro testing of the bactericidal effect is not particularly informative. Some studies suggest that the interior of the teat canal can be infected, and bacteria can multiply very easily in this very hospitable site for microorganism growth. Milk or milk residues in the test canal or other infected sites can provide a nutrient medium. To make in vitro testing more realistic, milk (e.g. skim milk) is sometimes added to the in vitro growth medium. Another approach to greater reliability for measuring bacteriostasis and/or kill rates is the "semi-in vivo" test, wherein preserved, excised teats collected from a slaughterhouse are dipped in a suspension of colony forming units and later treated with the teat dip. The more realistic tests sometimes suggest that an excellent in vitro kill may correlate poorly at best with effectiveness in the field. Field studies are, in the final analysis, the most definitive, but the semi-in vivo test can be a reasonable approximation of actual use.

SUMMARY OF THE INVENTION

It has now been discovered that, when the killing concentration of a teat dip preparation containing a nitroalkanol such as 2-bromo-2-nitropropane-1,3-diol was determined, applicant found that it lacked the ability to kill *Pseudomonas aeruginosa* even though the preparation was effective against *Staphylococcus aureus*. In contrast, it was further discovered that the bactericidal effect of a neutral-to-mildly acidic antibacterial composition having a nitroalkanol is markedly improved in semi-in vivo tests by the addition of an effective amount of a water soluble aminocarboxylic acid or aminocarboxylate chelating agent having a calcium chelate stability constant of at least about 6, the preferred chelating agent being a water soluble ethylenediamine tetraacetic acid salt, hereinafter referred to as an EDTA salt.

Accordingly, this invention contemplates a topically applied composition for the treatment of mastitis which comprises the nitroalkanol potentiated with the aminocarboxylic-type chelating agent and preferably containing an anionic sanitizer. Topical application by the conventional teat dip technique is preferred, and conventional ingredients can be added to the teat dip, e.g. emollients and water thickeners or thixotropes.

Topical mastitis-treating compositions of this invention, according to available test results, have excellent bactericidal properties against gram negative organisms such as *Pseudomonas aeruginosa*, and appear to provide relatively quick bactericidal action, e.g. an effective kill in 15 to 30 seconds. Furthermore, compositions according to the present invention have been found to have excellent bactericidal properties under neutral or mildly acidic conditions, e.g. a pH of 4 to 7, more preferably below 6.5. Including an anionic sanitizer appears to insure adequate activity against gram positive organisms at a pH below 7.

The constituents of the present invention can be prepared in either "dry form" and later added to water to form an aqueous solution thereof or can simply be mixed with water and marketed as an aqueous solution. To stabilize the pH of such a solution, a suitable buffering agent can be included.

DETAILED DESCRIPTION

In this application, the following terms have the indicated meanings:

"Uniformly distributable" means soluble or dispersible.

"EDTA" means ethylenediamine tetraacetic acid.

"EDTA salt" means a chemical compound in which one or more replaceable hydrogens or hydrogen cations of EDTA (i.e. the protons of the four —COOH groups which theoretically would be released by the reaction —COOH→—COO⊖+H⊕) have been replaced by a different cation, e.g. an alkali metal cation. The term "EDTA salt" is intended to include both preformed salts, which are blended with the other ingredients of compositions of this invention, and EDTA salts formed in situ, e.g. from the reaction of EDTA itself and alkali metal hydroxides or basic salts.

"EDTA$^{-4}$" means the ethylenediamine tetraacetate anion, i.e. the anion resulting when all the protons have been removed from all four carboxyl groups of the EDTA molecule.

"Bactericidal" means that the organism is killed as opposed to the term "bacteriostatic" which means that the growth of the organism is inhibited.

Components Used in the Compositions of this Invention

As noted previously, compositions of this invention are typically "teat dips" and will be described as such, though, of course, other methods of topical applications besdies teat-dipping might be used, if equally effective in killing bacteria. The nitroalkanols, EDTA salts and other aminocarboxylic-type chelating agents, anionic sanitizers, emollients, thickeners, and buffers of a typical teat dip will now be described in detail.

Nitroalkanols

Nitroalkanols suitable for use in the present invention are represented by the formula

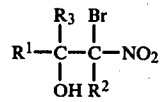

wherein $R_1$ is hydrogen, alkyl having 1 to 12 carbon atoms, and phenylalkyl of up to 10 carbon atoms, $R_3$ is hydrogen, or $R_1$ and $R_3$ together with the shared carbon atom form a cycloalkyl ring having 5 to 7 carbon atoms, and $R_2$ is hydrogen, methyl, ethyl, hydroxymethyl, or bromine. A non-exhaustive listing of nitroalkanols suitable for employment in antibacterial compositions according to the present invention and their properties can be found at column 1, line 31 to column 2, line 38 of the Clark et al U.S. Pat. (3,558,788), the disclosure of which is hereinafter incorporated by reference. All nitroalkanols are not equally effective, however, and the nitroalkanol most preferred in practicing the present invention is the nitroalkadiol 2-bromo-2-nitropropane-1,3-diol. In a composition useful as is for teat dipping, the amount of nitroalkanol used generally is within the range of 0.05 to 0.5% by weight of the total composition (including aqueous diluent medium). The optimum "use" concentration is 0.15% by weight - this level of concentration, suitably "potentiated" with an aminocarboxylic-type chelating agent, provides, at the least cost, a kill roughly comparable to the commercially available iodophor teat dips. Increasing the "use" concentration up to 0.5% may improve performance slightly, but will also increase costs. Beyond 0.5%, the improvement (if any) is believed to be not justified by the cost.

Ethylenediaminetetraacetic Acid (EDTA) Salts

Water soluble EDTA salts preferred in practicing the present invention are represented by the formula

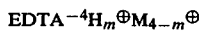

wherein EDTA$^{-4}$ is ethylenediaminetetraacetate, M+ is a topically acceptable cation such as an alkali metal or ammonium cation, and m is an integer from 0 to 3. Preferably, M+ is sodium or potassium with the most preferred EDTA salt being EDTA$^{-4}$H$_2$⊕Na$_2$⊕, although other sodium EDTA salts are commercially available, including the tetra sodium salt. The amount of the EDTA salt added to the composition according to the present invention should be sufficient to significantly increase the topical bactericidal effect of the nitroalkanol used against *Pseudomonas aeruginosa* organisms. Preferably, this amount is sufficient to insure destruction of substantially all of the *Pseudomonas aeruginosa* organisms on teat skin surfaces and in teat canals. IN a composition useful as is for teat dipping, the EDTA salt comprises 0.1 to 4% and most preferably 1% by weight of the total composition (including water). It appears that the EDTA salt improves the permeability of the cell wall to the bactericide, in this case the nitroalkanol. Although this invention is not bound by any theory, it is believed that the permeability of the cell wall is improved due to the fact that the EDTA salt removes calcium ions from the cell wall.

When aqueous teat dips containing a major amount of water are made up according to this invention, the EDTA salt may be partially inactivated by hardness in the water. Under such circumstances, the amount of EDTA salt included in the composition will be in excess of the amount needed to chelate water hardness, so that a hardness-free aqueous medium containing free, unchelated ethylenediaminetetraacetate anions is obtained. Less than 1% by weight of EDTA salt will tie up all the hardness in typical "hard" waters; accordingly, a 1 to 4% by weight level of EDTA will have at least some effectiveness in this invention almost regardless of water hardness. Also believed to be of major importance is the calcium-rich residual milk remaining on the teat or in the teat canal. This EDTA level will also tie up such calcium.

If tetrasodium or tetrapotassium EDTA is used as the EDTA salt, the buffer system (described subsequently) will ordinarily be designed to counter the pH-raising effect of such salts. Disodium EDTA has a much less pronounced pH-raising effect and is still sufficiently water soluble for use in the invention.

For the aforementioned theoretical reason, the M+ cation is monovalent. It is presently theorized that a polyvalent cation (particularly divalent cations such as those of the alkaline earth metals) could interfere with the chelating capacity of the EDTA salt. The chelate binding constant of EDTA/monovalent ion chelates can be very low—generally less than 5 and typically near zero. The EDTA/Ca chelate constant, on the other hand, is well above 5 (i.e. 10.6).

Since EDTA itself is only slightly soluble in water, its use in the present invention is not preferred, unless it is neutralized to an EDTA salt in situ, e.g. with an alkali metal hydroxide or a basic salt.

Other Aminocarboxylic Acids or Aminocarboxylates

Water soluble aminocarboxylic-type chelating agents having a calcium stability constant of at least about 6 (e.g. about 6 to about 13) appear to provide a "potentiating" effect similar to (and in some cases almost identical to) EDTA, though EDTA salts are still preferred for reasons of commercial availability, low toxicity, and wide acceptance in various arts such as the food and pharmaceutical arts. The preferred aminocarboxylic acid or aminocarboxylate chelating agents are at least tridentate, although, according to the scientific literature on bactericidal effects of aminocarboxylates, the bidentate iminodiacetic acid (IDA) should behave in a manner closely analogous to the tridentate nitrilotriacetic acid (NTA), one of the preferred chelating agents. At a pH below 7, it might be assumed that the $-COO^{\ominus}$ group is the most effective dentate substituent, and that hydroxyl-type dentates (e.g. of the hydroxyalkyl type) would be less effective; however, experimental data indicate that hydroxyaminocarboxylic or hydroxyaminocarboxylate chelating agents can be a fully effective type of aminocarboxylic or aminocarboxylate agent suitable for use in this invention, provided that the calcium stability constant is at least about 6. Surprisingly, however, the effectiveness of aminocarboxylic-type chelating agents in the context of this invention does not appear to depend entirely upon stability constants, since 3 to 5 minutes of treatment with a composition containing nitrilotriacetic acid (calcium stability constant=6.41) appeared to provide results comparable to aminocarboxylates having significantly greater calcium stability constants.

The aminocarboxylic-type chelating agents most effectively employed in this invention contain a substituted nitrogen atom or nitrilo group which is linked to the alpha carbon (alpha to the $-COO^{\ominus}$ substituent). In other words, the nitrogen atom typically has two or more monovalent acetic acid or ethanoate substituents ($-CZ_2COO^{\ominus}$, where Z can be H). A typical chelating agent of this type can be represented by the structural formula

$$R-N(CH_2COO^{\ominus})_2H_a{}^{\oplus}M_{2-a}{}^{\oplus}$$

wherein
R represents an organic residue,
a is 0 to 2, and
M+ is as defined previously.

The organic residue R can and preferably does contain additional aminocarboxylic-type chelating functionality, so that the chelating agent molecule will be at least tridentate in aminocarboxylic acids or aminocarboxylates. In the case of the bidentate IDA, R would be hydrogen; IDA is one of the most water soluble of the aminocarboxylic chelating acids. (As in the case of EDTA, the aminocarboxylate salts can be preformed or formed in situ by reaction with an alkali metal hydroxide or a basic salt.) Preferred examples of R are:

$-CH_2COO^{\ominus}$ and

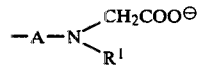

wherein A represents a divalent aliphatic or cycloaliphatic nucleus or a polyalkylene polyamine chain such as diethylenetriamine, including diethylenetriamine substituted with further dentates (e.g. ethanoates), and
$R^1$ is ethanoate ($-CH_2OO^{\ominus}$), lower hydroxyalkyl (e.g. $-CH_2CH_2OH$), or the like.

According to the scientific literature, chelating ability is not necessarily lost when organic groups (besides the nitrilo group) are substituted on the alpha carbon, i.e. $-CH_2COO^{\ominus}$ can be $-CRHCOO^{\ominus}$ or $-CR_2COO^{\ominus}$. For example, chelating agents such as N,N¹-ethylenebis(2-o-hydroxyphenol)glycine have been synthesized, wherein the dentate is $-NH-CH(\phi OH)-COO^{\ominus}$, $\phi$ representing a phenyl group.

Besides EDTA, the common aminocarboxylic acids with calcium chelate formation constants greater than 6 are:
nitrilotriacetic acid (NTA), hydroxyethylethylenediaminetriacetic acid (HEDTA),
cyclohexane-1,2-diaminotetraacetic acid (CDTA),
diethylenetriaminepentaacetic acid (DPTA), and
analogs of the foregoing such as triethylene tetramino polyacetic acids, other lower alkylene diamine tetraacetic acids (the term "lower" being understood to include carbon chains up to 6 carbons in length), analogs in which an acetic acid (ethanoate) dentate is replaced by a hydroxy-lower alkyl group, etc.

In other words, the preferred aminocarboxylic-type, polydentate chelating agents are the water soluble nitrilopolyacetic acids (and their water soluble salts) which have calcium chelate stability constants greater than about 6. Both mononitrilo- (e.g. NTA) and polynitrilo-polyacetic acids (e.g. EDTA, CDTA, HEDTA, DPTA, etc.) are operative in this invention, and the preferred polydentates are at least tridentate in chelating functional groups capable of chelating calcium in neutral and acidic media. Most typically, the nitrilopolyacetic acid, in its acetate form, contains the aminodicarboxylic or aminodicarboxylate bidentate grouping

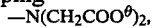
$-N(CH_2COO^{\ominus})_2$, and preferably at least one additional aminocarboxylate or aminocarboxylic dentate.

Representative calcium and magnesium chelate constants (from Chaberek et al, Organic Sequestering Agents, John Wiley and Sons, N.Y., N.Y., 1959) are set forth below.

| Agent | Stability Constants | |
|-------|---------------------|---|
|       | $Ca^{++}$ Chelate | $Mg^{++}$ Chelate |
| NTA   | 6.41  | 5.41  |
| EDTA  | 10.59 | 8.69  |
| HEDTA | 8.0   | 5.2   |
| CDTA  | 12.50 | 10.32 |

Anionic Sanitizers

If some activity against gram positive microorganisms may be safely sacrificed, the anionic sanitizer may be omitted from compositions of this invention. Ordinarily, however, the anionic sanitizer antimicrobial activity is greatly preferred to provide a margin of safety against some of the more virulent gram positive mastitis-causing bacteria (e.g. S. aureus). The anionic sanitizer tends to have maximum biocidal activity and/or biostatis at a pH below 7 and hence can be added to the composition in the acid form. For reasons which are presently not understood, the EDTA salt and the anionic sanitizer cooperate very effectively at mildly acidic pH's. It might be expected that there would be no mutually effective pH for both the anionic sanitizer and the EDTA, but experiments conducted with this invention do not presently confirm any such difficulty with the pH range.

Preferred anionic sanitizers have the formula
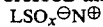
$LSO_x{}^{\ominus}N^{\oplus}$ wherein L is organic, typically an aromatic or aliphatic radical (including alkyl-aryl radicals), x is 3 or 4, and $N^{\oplus}$ is a topically acceptable cation such as a proton, an alkali metal cation, ammonium, or organic ammonium (e.g. triethanolammonium), an alkali metal cation or a proton being preferred. The preferred aromatic or aliphatic radicals are the linear alkyls and linear alkylaryls. All anionic sanitizers do not work with equal effectiveness, and linear alkylbenzene sulfonates presently appear to provide very adequate activity against S. aureus and the like at a pH near 5.

With respect to the linear alkyl chain, it should not be so long as to create incompatibility with water yet not so short so that skin irritation can become a problem. Therefore, the alkyl chains should preferably be 9 to 18 carbons in length. All sulfonates are not equally effective, the most preferred linear alkyl benzene sulfonic acid salt for use in connection with compositions of the present invention being sodium dodecylbenzenesulfonate. As is known in the art, the $C_{12}$ benzene sulfonates and the corresponding sulfonic acid are commercially available as mixtures with the $C_{14}$ and $C_{16}$ homologs and sometimes other homologs as well. The degree of purity of the $C_{12}$ species does not appear to be important in the context of this invention, and commercially available forms of the sulfonic acid and its salts are fully useful, without purification.

Emollients

Emollients incorporated into compositions of the present invention can serve to replace some of the natural skin oil lost by the milking process and/or to assist in forming a protective coating on the skin. An emollient which has a soothing action on teat skin, preferably by a humectant action; which is compatible with aqueous solutions of EDTA salts and antimicrobial brominated nitroalkadiols, such as 2-bromo-2-nitropropane-1,3-diol; and which does not significantly detract from the antimicrobial action of the nitroalkanol/EDTA-salt teat dip can be utilized in this invention. Liquid, oily organic emollients (e.g. polyols with relatively high boiling points, typically above 100° C. at 1 atmosphere) are preferred, but water soluble or water dispersible solids such as polyvinyl pyrrolidone or sorbitol have been used effectively in known teat dip formulas. Sorbitol takes up moisture under some conditions and is thus believed to provide an emollient action similar to liquid polyols. In addition to polyvinyl pyrrolidone (PVP) and the emollients used in "SURGE" (trademark), other well known emollients can be found at column 2, lines 30–43 of the patent to Caughman et al, U.S. Pat. No. 3,933,777, issued Nov. 23, 1976, the disclosure of which is incorporated by reference. All emollients do not work with equal effectiveness, and a preferred emollient for use in practicing the present invention is glycerine. The amount of the emollient in a composition suitable for use as is for teat dipping should be in the range of from 0.1 to 10%, most preferably about 8% by weight of the total composition (including aqueous diluent). Amounts up to about 20% by weight of emollient can be used (see U.S. Pat. No. 4,025,628, Table I) but such amounts are not believed to be necessary in the context of this invention. Another type of preferred emollient is the liquid anionic polyfunctional surface active agent sold under the trade name Rewoderm S-1333 (trade name Rewo Chemical, Incorporated, Farmingdale, L.I., New York, 11735, U.S.A.). This emollient is said to be effective for use with anionic surfactants. While the chemical nature of this product has not been disclosed, it is believed to be substantive to the skin and either prevents moisture loss or is a humectant or both. An emollient such as Rewoderm S-1333 is also an effective additive to the composition of the present invention.

The Aqueous Diluent

As disclosed in U.S. Pat. No. 4,025,628, cited previously, powdered, storage stable water-soluble or water dispersible emollient-antimicrobial formulas can be mixed with water on the job to make an active teat dip. This procedure avoids the need to ship a large amount of aqueous diluent to the end-user. As will be apparent to those skilled in the art, a liquid concentrate could be an alternative to the dry powder approach described in the U.S. Pat. No. 4,025,628 patent. Many dairy farmers purchase readily available laundry-type liquid bleaches (such as 4% aqueous sodium hypochlorite) and use them as concentrates for teat dipping—the common practice being to dilute the liquid laundry bleach with plain water prior to use.

Water is suitable as a diluent in compositions of this invention, since commercially available aminocarboxylate salts (such as sodium salts) and suitable commercially available nitroalkanols (such as 2-bromo-2-nitropropane-1,3-diol) dissolve readily in water; furthermore, water has unquestionable economic advantages over organic liquid diluents. The preferred aqueous diluent used in this invention is water thickened with a thickening agent or thixotrope.

When compositions of this invention are at a concentration suitable for their end use (as opposed to a dry state or liquid concentrate state), the water phase makes up the major amount by weight of the total composition. Typically, more than 75% by weight of the composition will be water or other pharmaceutically inactive ingredients. In order to allow for at least about a percent by weight of emollient and at least about a percent by weight of buffers, thickening agents, and topically active agents such as the sulfonate, the nitroalkanol, and the EDTA salt, it is preferred that the amount of water in the "use" concentration be less than 98% by weight. Typical amounts of water used in such end use concentrations range from about 80 to 95% by weight; if a full 8% by weight of emollient is used, the water content will be less than 92% by weight.

Thus, if the composition is either in dry or concentrate form, the ratio of dilution with plain water will normally be less than 100:1 by weight (water:solids), more typically less than 20:1. For the end user, a volume:volume or volume:weight (water:solids) dilution step would normally be more convenient. Particularly in the case of a concentrate, the dilution ratio would be approximately the same as for a weight:weight dilution. To dilute dry solids, the dilution ratio would virtually always be greater than 2:1 by weight.

In most cases, the most reliable bench mark for dilution with water is the nitroalkanol; that is, sufficient water should be added to reduce the concentration of the nitroalkanol to the minimum effective level, since the nitroalkanol is ordinarily the most expensive ingredient in the composition. For typical teat dip applications, a liter (1,000 ml) of solution is a more-than-adequate amount to provide full immersion of the animal's teat in the dip, and an amount of solution within the range of 100–500 ml can be sufficient. To prepare approximately this amount of solution, from about 1 to 1,000 mg of the nitroalkanol would ordinarily be used, e.g. about 100 mg. For each part by weight of the nitroalkanol, a dry formula would typically contain 0.1–5 aprts by weight of linear alkyl benzene sulfonate, 0.5–10 parts by weight of EDTA salt, up to about 80 parts by weight of emollient, and amounts of thickener and buffer suitable for providing the desired viscosity (or shear-dependent viscosity) and pH. It must be remembered that, if water is to be added to a concentrate or a dry formula, the pH of tap water can vary with hardness and other factors. Hard water with a pH approaching 10 is known, as is water with a pH on the slightly acid side. Softened, deionized, distilled, or neutral water is preferred for use in this invention, although a well-designed buffer system can take care of fluctuations in pH which might be introduced by slightly alkaline tap water. As will be apparent from the discussion of the function of the aminocarboxylic-type chelating agent, water containing calcium or magnesium "hardness" could have a minor but nevertheless detrimental effect upon the efficacy of the composition.

A well-controlled product containing a fully effective aminocarboxylate/nitroalkanol combination can be provided by the simple expedient of pre-diluting the composition to the "use" concentration and marketing it in this form. In this manner, the manufacturer can better control the degree of hardness (if any) in the aqueous diluent and can instruct the user to make no further dilution or add any extraneous ingredients. For this reason, the preceding and following discussions of amounts of key ingredients of the composition are generally based upon the total composition, including aqueous diluent, at the "use" concentration.

Water Thickening Agents or Thixotropes

As is well known in the art, a variety of organic and inorganic agents can increase the viscosity, apparent viscosity, or shear-dependent viscosity (thixotropy) of water. Inorganic types include clays such as bentonite, fumed silica, and the like. If desired, clays can be treated with organic coatings. Typical of the organic thickeners are a variety of cellulosic (including modified cellulosic) compounds, e.g. hydrophilic cellulosic esters and ethers. Other typical known thickening agents for water are disclosed at column 3, lines 19–40 of the Caughman et al U.S. Pat. No. 3,993,777, the disclosure of which is hereby incorporated by reference. All thickeners do not work with equal effectiveness in this invention, the preferred ones being the cellulosic type, e.g. carboxymethyl cellulose (CMC). A fraction of a percent by weight of such thickeners can increase the viscosity measurement to more than several hundred centipoise. A few percent can thicken water to several thousand centipoise. An important aspect of this thickening is that the teat dip formula is fluid enough for pouring or dipping but still has sufficient thixotropy or viscosity to resist rapid draining or running off from the teat or udder. More than 0.1% by weight of thickener (based on the total composition) provides a thickening effect, while 20 weight-% or more may cause too much thickening. Optimum results are provided with about one part by weight of thickener to each 50–100 parts of water in the end-use composition.

Buffering Agents

As noted previously, the composition according to the present invention is most suitable for use as a teat dip when in the form of an aqueous solution containing a major amount of thickened water. Even if neutral, softened, distilled, or deionized water is used, adjustment of the pH of teat dip to less than 7.0 and stabilization of the pH with a buffer are desired. The pH of aqueous solutions of compositions according to the present invention preferably approximate skin pH, e.g. a pH above about 4 but less than about 6.5. A buffer system found by applicant to be suitable for maintaining the pH at or near 5 (e.g. within about a pH unit) is a citrate-citric acid buffer. Other buffer systems can be used, however, the main requirement for the buffering agent used being that it be physiologically compatible with the skin, compatible with the other ingredients of the composition, and not detrimental with respect to the bactericidal efficacy of the composition. The citrate of the citric acid buffer is preferably the salt of a monovalent metal base such as an alkali metal hydroxide.

The presently preferred pH is about 5 (determined at 23° C.). Efficacy roughly comparable to commercially available iodophor teat dips has been observed at this pH. Such efficacy is difficult to explain in view of the EDTA studies cited previously, but is nevertheless believed to have been substantiated by the presently available data from tests conducted in the course of developing this invention. Although this invention is not bound by any theory, the aminocarboxylic-type chelating agent and the anionic sanitizer may, it is felt, cooperate at a pH below 7.

Other Ingredients

As is known in the art of bactericidal compositions, colorants (e.g. dyes or pigments), odorants, extenders, diluents, and other non-essential or optional ingredients can be included in teat dip formulas and thus can be utilized (if desired) in compositions of this invention. Colorants are particularly desirable for aesthetic reasons and are also added for convenience in identifying a product from among a number of products which a dairy farmer may have in the milk-house.

Method

Compositions according to the present invention have been found to be particularly effective when used as a teat dip, though spraying or swabbing onto the teats might be expected to have somewhat similar bactericidal effects if the contact time is about the same. Preferably, the teats of the animal are dipped in a reservoir or receptacle containing a thickened aqueous teat dip of the present invention with the excess being then allowed to drip freely when the source is removed. The high viscosity of the teat dip ensures a contact time greater than a second, e.g. 15 seconds to 15 minutes. In the teat dip approach, the "use" concentrations of key ingredients of compositions of this invention are preferably used, as explained previously. As also explained previously, pre-dilution to the "use" concentration by the manufacturer of the teat dip is preferred.

EXAMPLES 1–4

In accordance with this present invention, four formulations (Examples 1 through 4) were made up with different levels of linear alkyl benzene sulfonate, 2-bromo-2-nitropropane-1,3-diol, emollient and buffer; all four Examples had the same level of disodium EDTA. A "Reference A" sample was prepared which was similar to Example 3 except that it contained no EDTA salt. The formulas of the Examples and the "Reference A" are set forth below:

| Ingredients | Ex 1 | Ex 2 | Ex 3 | Ex 4 | Reference A |
|---|---|---|---|---|---|
| Linear alkyl benzene sulfonate | 3.500 | 2.500 | 1.500 | 0.500 | 1.500 |
| 50% NaOH | 0.860 | 0.614 | 0.369 | 0.123 | 0.369 |
| EDTA, disodium salt | 1.000 | 1.000 | 1.000 | 1.000 | — |
| Glycerine | 5.000 | 5.000 | 5.000 | 5.000 | 5.000 |
| Carboxymethyl cellulose | 1.000 | 1.000 | 1.000 | 1.000 | 1.000 |
| Citric acid | 0.100 | 0.100 | 0.100 | 0.100 | 0.100 |
| Sodium citrate | 0.400 | 0.400 | 0.400 | 0.400 | 0.400 |
| Color (F,D, and C No. 1) | 0.018 | 0.018 | 0.108 | 0.018 | 0.018 |
| 2-Bromo-2-nitropropane-1,3-diol | 0.150 | 0.150 | 0.150 | 0.150 | 0.150 |
| Water | 87.972 | 89.218 | 90.463 | 91.709 | 91.463 |
| pH | 5.0 | 5.0 | 5.0 | 5.0 | 5.0 |

The samples were prepared by first dispersing the carboxymethyl cellulose in water with vigorous stirring and adding other components in the order shown avoiding excess foam formation.

After screening for emollient and other properties, the product of Example 3 and the Reference A were tested for their bacterial properties against *Staphylococcus aereus* and *Pseudomonas aeruginosa*, as follows: fifty ml samples of the teat dip preparations at room temperature (approximately 22° C.) were inoculated with approximately $1 \times 10^6$ cells of the test organism (diluted, 24 hour broth culture) and mixed thoroughly. After various exposure periods, one loopful (4 mm diameter) of the inoculated mixture was subcultured into letheen broth and incubated for 48 hours in a 37° C. incubator. At the end of this incubation period, the subcultures were visually examined for growth or no growth. The results are summarized in Table 1.

Table 1

BACTERICIDAL TESTS ON TEAT DIP PREPARATIONS

| Product | Test Organism | Exposure Times | | | | | | |
|---|---|---|---|---|---|---|---|---|
| | | 15 sec | 30 sec | 1 min | 2 min | 5 min | 10 min | 15 min |
| Reference | Staph. aureus | + | + | 0 | 0 | 0 | 0 | 0 |
| | Ps. aeruginosa | + | + | + | + | + | + | + |
| Example 3 | Staph. aureus | + | 0 | 0 | 0 | 0 | 0 | 0 |
| | Ps. aeruginosa | + | 0 | 0 | 0 | 0 | 0 | 0 |

+ = growth
0 = no growth
(The Reference A sample is identical with the product of Example 3 except that Example 3 contained disodium EDTA and the Reference a contained no EDTA.)

The results shown in Table 1 indicate that the Reference A sample possessed good activity against *Staphylococcus aureus*, a gram positive bacterium, as expected but did not possess a high degree of activity against *Pseudomonas aeruginosa*, a gram negative bacterium. The addition of ethylene diamine tetra acetic acid salt markedly enhanced the bactericidal performance against *Pseudomonas aeruginosa* giving no growth, i.e. no growth forming units per loopful, after 30 seconds of exposure.

EXAMPLE 5

Example 5 is illustrative of further improvement to the composition shown in Example 3 and in particular in respect to its emollient properties. In-farm tests have indicated that Example 5 is superior to Example 3 in its emollient properties and this improvement is believed to be due to the increased glycerine contents as well as incorporation of a polyfunctional anionic surfactant sold under the trade name of Rewoderm*. It was added to counteract any defatting tendency of the common anionic surfactant.

*Rewoderm, manufactured by Rewo Chemical, Inc., Farmingdale. L.I., New York

The composition of Example 5 and its corresponding Reference samples to which Example 5 was compared are set forth below:

| Ingredients | Ex. 5 | Ref. B | Ref. C | Ref. D | Ref. E |
|---|---|---|---|---|---|
| Linear alkyl benzene sulfonate | 2.000 | — | — | — | 2.000 |
| 50% NaOH | 0.100 | 0.100 | 0.100 | 0.100 | 0.100 |
| EDTA, disodium salt | 1.000 | — | 1.000 | 1.000 | — |
| Glycerine | 8.000 | 8.000 | 8.000 | 8.000 | 8.000 |
| Rewoderm S-1333 | 0.250 | 0.250 | 0.250 | 0.250 | 0.250 |
| Carboxymethyl cellulose | 1.500 | 1.500 | 1.500 | 1.500 | 1.500 |
| Citric acid | 0.124 | 0.124 | 0.124 | 0.124 | 0.124 |
| Sodium citrate | 0.100 | 0.100 | 0.100 | 0.100 | 0.100 |
| Color (F,D, & C No. 1) | 0.014 | 0.014 | 0.014 | 0.014 | 0.014 |
| 2-Bromo-2-nitropropane-1,3-diol | 0.150 | 0.150 | — | 0.150 | 0.150 |
| Water | 86.762 | 89.762 | 88.912 | 88.762 | 87.762 |
| pH | 5.0 | 5.0 | 5.0 | 5.0 | 5.0 |

In a simulated use evaluation, the effectiveness of the product of Example 5 was compared against the effectiveness of a number of different Reference samples designated References B, C, D, and E respectively. In this evaluation, the effectiveness was determined by a "semi-in vivo test". Briefly described, excised teats are collected from cows at a slaughter house, refrigerated and transported to the laboratory, trimmed, washed and otherwise prepared for the test. The teats (set of 10 for each product tested) are dipped in a bacterial suspension containing $1 \times 10^8$ colony forming units (CFU)/ml to a depth of 15 mm and allowed to drain for 5 minutes after which the teats are dipped to a depth of 30 mm in the test product and allowed to drain for 10 minutes to simulate a teat dip product in use.

Organisms surviving this treatment are removed by rinsing with 5 ml of solution containing an appropriate neutralizer from a polyethylene wash bottle and collected in a sterile vial. This collected rinse solution is surface plated-out on an appropriate agar medium in 0.1 ml amount. Appropriate dilutions of the collected rinse solution are made in which a high count is expected. The "control" (base) count is established by treating a set of ten teats in the same manner, but omitting exposure to the teat dip product, allowing the teats to drain for 15 minutes and rinsing off the teat as for the test teats by making appropriate dilutions and surface plating a sample on an appropriate agar medium. The geometric mean of the microorganisms recovered from the ten teats is multiplied by 50 and by an appropriate reciprocal of the dilution factor to obtain the bacteria count recovered per teat. The reduction of bacteria by the teat dip treatment is expressed in percent reduction as well as the log order of the reduction. The comparative effectiveness against Ps. aeruginosa between the product of Example 5 and the various Reference samples designated B, C, D and E are summarized in Table 2.

Table 2

COMPARATIVE EFFECTIVENESS OF PRODUCT OF EXAMPLE 5 AND THEIR CORRESPONDING REFERENCE SAMPLES B, C, D & E AGAINST PS. AERUGINOSA

| Product | Reduction from Control* | |
|---|---|---|
| | — log Reduction | % Reduction |
| Product of Ex. 5 | 1.79 | 98.4 |
| Reference B | 1.18 | 93.3 |
| Reference C | 1.17 | 93.2 |
| Reference D | 1.40 | 96.0 |
| Reference E | .61 | 76.3 |

*— log Reduction = $\log \frac{\text{Count of treated teats}}{\text{Count of untreated teats (control)}}$ % Reduction = $100 - \frac{\text{Count of treated teats}}{\text{Count of untreated teats}} \times 100$ The results summarized in Table 2 indicate that the product of Example 5 out-performed all of the Reference samples B, C, D, and E, lacking in one or more of the key ingredients present in the product of Example 5. It is of significance to note that the Reference sample E containing the linear alkyl benzene sulfonate and 2-bromo-2-nitropropane-1,3-diol performed similarly to the commercial product containing 2-bromo-2-nitropropane-1,3-diol. (See Table 3, Product L.) Comparing Reference sample E (Product of Example 5 less linear alkyl benzene sulfonate and EDTA) it would appear that there is a slight incompatibility between the alkyl benzene sulfonate and the 2-bromo-2-nitropropane-1,3-diol. The addition of EDTA to the system appeared not only to overcome such incompatibility but substantially enhanced the overall performance as shown by the result of Example 5.

In another simulated use evaluation, the effectiveness of the product of Example 5 was compared against the effectiveness of a number of different commercially available or known teat dip products. The results of this comparison are summarized in Table 3.

Although data is available regarding the effectiveness of the commercially available products against Ps. aeruginosa, such data is not available for the product of Example 5. Accordingly, the data in Table 3 are limited to S. aureus and S. agalactiae.

TABLE 3

COMPARATIVE EFFECTIVENESS OF PRODUCT OF EXAMPLE 5 AND VARIOUS PROPRITARY TEAT DIP PRODUCTS

| | | | Staph. aureus | | | Strept. agalactiae | | |
|---|---|---|---|---|---|---|---|---|
| | | | | Reduction from Control | | | Reduction from Control | |
| Product | Active Ingredient Type | % Active Ingredient | Geometric Mean No. Recovered | % | —Log | Geometric Mean No. Recovered | % | —Log |
| Control | | | 3,504,500 | | | 3,184,000 | | |
| A | Iodophor | 1.0 | 3 | 99.99 | 6.06 | 3 | 99.99 | 6.03 |
| B | Iodophor | 1.0 | 9 | 99.99 | 5.59 | 19 | 99.99 | 5.23 |
| C | Iodophor | 0.5 | 7 | 99.99 | 5.69 | 8 | 99.99 | 5.61 |
| D | Sodium Hypochlorite | 4.2 | 3 | 99.99 | 6.06 | 1 | 99.99 | 6.51 |
| E | Sodium Dichloro-S-triazinetrione | 0.6 | 35 | 99.99 | 5.00 | 16 | 99.99 | 5.31 |
| F | Quat. Ammonium Chloride | 0.18 | 371 | 99.99 | 3.97 | 26 | 99.99 | 5.09 |
| G | Chlorohexidine | 0.5 | 1,252 | 99.96 | 3.46 | 25 | 99.99 | 5.11 |

TABLE 3-continued
COMPARATIVE EFFECTIVENESS OF PRODUCT OF EXAMPLE 5 AND VARIOUS PROPRITARY TEAT DIP PRODUCTS

| Product | Active Ingredient Type | % Active Ingredient | Staph. aureus Geometric Mean No. Recovered | Reduction from Control % | −Log | Strept. agalactiae Geometric Mean No. Recovered | Reduction from Control % | −Log |
|---|---|---|---|---|---|---|---|---|
| H | Hexachlorophene | * | 600,395 | 82.87 | 0.76 | 699,715 | 78.02 | 0.65 |
| I | Cetyl Pyridium Chloride | 0.2 | 2,043 | 99.94 | 3.23 | 655 | 99.98 | 3.69 |
| J | 8-Hydroxy Quinoline Sulfate | 0.1 | 251,530 | 92.82 | 1.14 | 5,165 | 99.83 | 2.80 |
| K | Pine Oil | * | 94,205 | 97.31 | 1.57 | 138,970 | 95.64 | 1.36 |
| L | 2-Bromo-2-Nitropropane-1,3-Diol | 0.2 | 24,497 | 99.30 | 2.15 | 46,054 | 98.55 | 1.85 |
| Product of Ex. 5 | 2-Bromo-2-Nitropropane-1,3-Diol | 0.15 | 20 | 99.99 | 5.24 | 5 | 99.99 | 5.8 |

*Hexachlorophene and pine oil were presumably the respective active ingredients in these products.

The results of Table 3 indicate that the product of Example 5 is equally as effective as Iodophor preparations containing 1.0% iodine, against S. aureus and S. agalactiae, i.e. product A and B, and is equally effective as 4.2% sodium hypochlorite, i.e. product D, and a product containing 0.6% sodium dichloro-S-triazinetrione, i.e. product E. It will be noted that the quaternary ammonium chloride based products, i.e. products F and I, were less effective than the active halogen products. The remainder of the products, i.e. products H, J and K were relatively ineffective as a teat dip. It will further be noted that product L containing a higher level of 2-bromo-2-nitropropane-1,3-diol than the product of Example 5 was less effective than Example 5. The difference in performance between product L and the product of Example 5 is believed to result from the inclusion of the EDTA salt in the product of Example 5.

In summary, the product of Example 5 combines the mildness of a non-halogen teat dip with the effectiveness of the halogen type products, offering a combination of properties hitherto unavailable to dairy farmers. Furthermore, the iodine contamination of milk is not possible with the Example 5 formulation.

EXAMPLES 6-9

Additional Examples and a Reference (Reference M) similar to Examples 1-5 and Reference A are set forth below. The pH was 5.0 for Reference M (formula without EDTA) and all four additional Example formulations. All amounts in the following Table are in parts by weight.

indicated previously in the discussion of other aminocarboxylic-type chelating agents.

| Ingredients | Parts by Weight |
|---|---|
| Aminocarboxylic-type chelating agent | 1.0 |
| Linear alkyl benzene sulfonate | 2.0 |
| 50% NaOH | Q.S. to pH 5.0 |
| Glycerine | 8.0 |
| Carboxymethyl cellulose | 1.5 |
| 50% Citric acid | 0.397 |
| "REWODERN" (see Example 5) | 0.25 |
| Color (F, D, and C No. 1) | 0.014 |
| 2-Bromo-2-nitropropane-1,3-diol | 0.15 |
| Water | Q.S. to 100 |
| pH | 5.0 |

The aminocarboxylic-type chelating agents used in these Examples were as follows:

| Example | Agent | Formula |
|---|---|---|
| 10 | HEDTA | (HOOCCH$_2$)CH$_2$CH$_2$N(CH$_2$CH$_2$OH)(CH$_2$COOH) |
| 11 | CDTA | C$_6$H$_{10}$[N(CH$_2$COOH)$_2$]$_2$ |
| 12 | NTA | N(CH$_2$COOH)$_3$ |

| Ingredients | Reference M | Example 6 | Example 7 | Example 8 | Example 9 |
|---|---|---|---|---|---|
| Linear alkyl benzene sulfonate | 2.0 | 2.0 | 3.0 | 3.5 | 4.0 |
| 50% NaOH | 0.193 | 0.193 | [Q.S. (quantity sufficient) to pH 5] | | |
| EDTA, disodium salt | — | 1.0 | 1.5 | 1.75 | 2.0 |
| Glycerine | 8.0 | 8.0 | 8.0 | 8.0 | 8.0 |
| Carboxymethyl cellulose | 1.5 | 1.5 | 1.5 | 1.5 | 1.5 |
| 50% Citric acid | 0.397 | 0.397 | 0.397 | 0.397 | 0.397 |
| "REWODERN" (see Example 5) | 0.25 | 0.25 | 0.25 | 0.25 | 0.25 |
| Color (F, D, and C No. 1) | 0.014 | 0.014 | 0.014 | 0.014 | 0.014 |
| 2-Bromo-2-nitropropane-1,3-diol | 0.15 | 0.15 | 0.225 | 0.26 | 0.3 |
| Water | [Q.S. (quantity sufficient) to 100 parts by weight] | | | | |

EXAMPLES 10-12

The following general formulations illustrate the use of NTA, HEDTA, and CDTA in place of EDTA. The terms NTA, HEDTA, and CDTA have the meanings Bactericidal Tests on Products of Reference M and Examples 6 Through 12

Bactericidal performance tests were performed against *Pseudomonas aeruginosa* using generally the procedure indicated for Examples 1 through 4. Notable differences in the test procedures were as follows: the inocula consisted of a 24 hour broth culture (nutrient broth). In the test summarized in Table 4, 1 ml of the 24 hour broth culture was added to 50 ml sample of the various test products at 22° C. (room temperature) and mixed thoroughly. After exposure periods of 30 seconds, 3 minutes and 5 minutes, 1 ml sample of this mixture was transferred to 9.0 ml of letheen neutralizer mixed thoroughly and further diluted to give $10^2$, $10^4$ and $10^5$ dilutions in sterile buffered water. Appropriate samples of dilutions were then transferred and plated out in tripticase soy agar, incubated for 48 hours at 37° C. and the colonies developed thereon counted. This data is summarized in Table 4.

In another test, the broth culture was centrifuged, and the centrifuged cells were resuspended in sterile skim milk; this suspension was used in place of the nutrient broth suspension and is believed to more nearly simulate the microorganism encountered under use conditions. In other respects, the test conditions were identical to those indicated for the data of Table 4. The results of this test are summarized in Table 5.

Table 4

Bactericidal Test Against *Pseudomonas aeruginosa* Broth Cultures

| Product | Organism Recovery (After Specified Exposure Times) | | |
|---|---|---|---|
| | 30 sec. | 3 min. | 5 min. |
| Control (buffered water) | $5.7 \times 10^6$ | $6.4 \times 10^6$ | $5.5 \times 10^6$ |
| Ref. M | $2.3 \times 10^6$ | $5.9 \times 10^6$ | $1.9 \times 10^5$ |
| Example 6 (EDTA) | $1.4 \times 10^4$ | $2.7 \times 10^3$ | $7.0 \times 10^2$ |
| Example 10 (HEDTA) | $5.1 \times 10^4$ | $2.5 \times 10^4$ | $1.2 \times 10^4$ |
| Example 11 (CDTA) | $2.6 \times 10^3$ | $<100$* | $<100$ |
| Example 12 (NTA) | $5.2 \times 10^5$ | $8.7 \times 10^3$ | $9.0 \times 10^2$ |

*A count of $<100$ simply indicates a zero colony count at $10^2$ dilution.

Table 5

Bactericidal Test Against *Pseudomonas aeruginosa* Resuspended in Milk

| Product | Organism Recovery (After Specified Exposure Times) | | |
|---|---|---|---|
| | 30 sec. | 3 min. | 5 min. |
| Control (buffered water) | $5.8 \times 10^6$ | $5.8 \times 10^6$ | $7.5 \times 10^6$ |
| Ref. M | $2.9 \times 10^6$ | $1.2 \times 10^6$ | $3.0 \times 10^5$ |
| Example 6 (1% EDTA) | $2.4 \times 10^5$ | $2.3 \times 10^4$ | $5.0 \times 10^3$ |
| Example 7 (1.5% EDTA) | $<100$* | $<100$ | $<100$ |
| Example 8 (1.75% EDTA) | $<100$ | $<100$ | $<100$ |
| Example 9 (2% EDTA) | $<100$ | $<100$ | $<100$ |
| Example 10 (1% EDTA) | $<100$ | $<100$ | $<100$ |
| Example 11 (1% CDTA) | $2.2 \times 10^4$ | $<100$ | $<100$ |
| Example 12 (1% NTA) | $4.0 \times 10^5$ | $<100$ | $<100$ |

*A count of $<100$ simply indicates a zero colony count at $10^2$ dilution.

What is claimed is:

1. An antibacterial composition, comprising:
   (a) a nitroalkanol of the formula

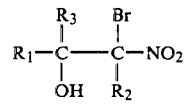

wherein $R_1$ is selected from the group consisting of hydrogen, alkyl having 1 to 12 carbon atoms, phenyl alkyl of up to 10 carbon atoms, and, together with $R_3$, $R_1$ and $R_3$ can be the residue of a cycloalkyl ring having 5 to 7 carbon atoms, including the shared carbon atom; $R_3$, if not part of the said residue, is hydrogen; and $R_2$ is selected from the group consisting of hydrogen, methyl, ethyl, hydroxymethyl, and bromine;

(b) an aminocarboxylic acid or aminocarboxylate chelating agent having a calcium chelate stability constant of at least about 6; said chelating agent being combined with said nitroalkanol in an amount sufficient to significantly increase the topical bactericidal effect, in nonalkaline aqueous solution, of said nitroalkanol against *Pseudomonas aeruginosa* organisms.

2. An antibacterial composition according to claim 1 wherein said nitroalkanol is 2-bromo-2-nitropropane-1,3-diol.

3. An antibacterial composition according to claim 1 wherein said chelating agent is selected from the topically acceptable carboxylate salts of a nitrilopolyacetic acid selected from the group consisting of EDTA, CDTA, HEDTA, and NTA.

4. An antibacterial composition according to claim 1 wherein said chelating agent comprises an ethylenediaminetetraacetate of the formula $H_m^+M_{4-m}^+EDTA^{-4}$, wherein $EDTA^{-4}$ represents the ethylenediaminetetraacetate anion,
   $M^+$ represents a topically acceptable cation, and
   m represents an integer from 0 to 3.

5. An antibacterial composition according to claim 2 wherein said composition comprises a major amount of water, said nitroalkanol being dissolved in said water; the amount of thus-dissolved nitroalkanol ranging from 0.05 to 0.5% by weight, based on the total composition.

6. An antibacterial composition according to claim 1 wherein said $M^+$ is an alkali metal cation.

7. An antibacterial composition according to claim 6 wherein said ethylenediaminetetraacetate comprises the disodium salt of ethylenediaminetetraacetic acid.

8. An antibacterial composition according to claim 5 wherein said amount of said ethylenediaminetetraacetate ranges from 0.1 to 4% by weight, based on the total composition.

9. An antibacterial composition according to claim 1 further comprising a compound uniformly distributable in water and having the general formula

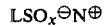

wherein L is organic, x is 3 or 4, and $N^\oplus$ is a topically acceptable cation.

10. An antibacterial composition according to claim 5 wherein the pH of said composition is greater than 4 but less than 6.5 at 23° C.

11. An antibacterial composition according to claim 10 further comprising a buffering agent to stabilize the pH of said composition at about 5, and an effective amount of an emollient.

12. An aqueous teat dip comprising the composition of claim 1, said composition including a thickener for increasing the viscosity of water.

13. An antibacterial composition, said composition having a pH above 4 and below 6.5 and containing a major amount of water, said composition comprising:
(a) 0.05 to 0.5% by weight of 2-bromo-2-nitropropane-1,3-diol;
(b) 0.1 to 4% by weight of an ethylenediaminetetraacetate of the formula $H_m{}^+M_{4-m}{}^+EDTA^{-4}$, wherein
EDTA$^{-4}$ represents the ethylenediaminetetraacetate anion,
$M^+$ represents a topically acceptable cation, and m represents an integer from 0 to 3;
(c) 0.5 to 5% by weight of a compound selected from the group consisting of linear alkylbenzene sulfonic acid and its alkali metal salts;
(d) substantially the balance of said composition being an aqueous diluent; said components (a), (b), and (c) being uniformly distributed through said aqueous diluent.

14. A composition according to claim 13 wherein said aqueous diluent is substantially hardness-free, and said composition further comprises:
(e) 0.1 to about 10% by weight of emollient;
(f) a thickening amount of a cellulosic water-thickening agent; and
(g) a buffering amount of a citrate/citric acid buffer, sufficient to provide a buffered pH in the said pH range.

15. An aqueous antibacterial composition having a pH of about 5 at 23° C., comprising:
2-bromo-2-nitropropane-1,3-diol in an amount of 0.15% by weight;
disodium ethylenediaminetetraacetate in an amount of about 1.0 to about 2.0% by weight;
$C_9$ to $C_{18}$-linear alkylbenzene sulfonate in an amount of from 0.5 to 3.5% by weight;
glycerin in an amount of 0.1 to 10% by weight;
carboxymethylcellulose in an amount of 1.5% by weight;
water in an amount of from about 80 to about 92% by weight; and
a citric acid-citrate buffer in an amount sufficient to stabilize said pH.

16. A method for killing organisms including *Pseudomonas aeruginosa* on an animal's teats comprising the steps of treating the teats of the animal with an aqueous medium containing a nitroalkanol of the formula

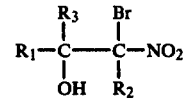

wherein $R_1$ is selected from the group consisting of hydrogen, alkyl having 1 to 12 carbon atoms, phenyl alkyl of up to 10 carbon atoms, and, together with $R_3$, $R_1$ and $R_3$ can be the residue of a cycloalkyl ring having 5 to 7 carbon atoms, including the shared carbon atom; $R_3$, if not the part of the said residue, is hydrogen; and $R_2$ is selected from the group consisting of hydrogen, methyl, ethyl, hydroxymethyl, and bromine and an aminocarboxylic acid or aminocarboxylate chelating agent having a calcium chelate stability constant of at least about 6, said chelating agent being present in an amount sufficient to significantly increase the topical bactericidal effect of said nitroalkanol against *Pseudomonas aeruginosa* organisms.

17. A method according to claim 16 wherein said aqueous medium has sufficient viscosity to resist rapid draining from the animal's teats, whereby a contact time with the teats in excess of 15 seconds is assured.

18. A method for killing organisms including *Pseudomonas aeruginosa* on an animal's teats comprising the step of dipping the teats of the animal in a reservoir of the composition of claim 15.

19. A method according to claim 16 wherein said treatment step comprises the step of dipping the teats in a reservoir of said aqueous solution.

20. A method for control of bovine mastitis with a teat dip comprising the step of dipping the bovine teats in an aqueous treatment medium, wherein said aqueous treatment medium comprises the composition of claim 13.

* * * * *

UNITED STATES PATENT AND TRADEMARK OFFICE
CERTIFICATE OF CORRECTION

PATENT NO. : 4,199,602

DATED : April 22, 1980

INVENTOR(S) : Steven E. Lentsch

It is certified that error appears in the above-identified patent and that said Letters Patent are hereby corrected as shown below:

```
Column 1, line 15, for "test" read --teat--.
Column 1, line 20, for "test" read --teat--.
Column 1, line 36, for "tests" read --teats--.
Column 2, line 57, for "growth-after" read --growth after--.
Column 4, line 31, for "partiuclar" read --particular--.
Column 4, line 59, for "test" read --teat--.
Column 6, line 13, for "besdies" read --besides--.
Column 6, line 25, for "R1" read --R₁--.
Column 7, line 7, for "IN" read --In--.
Column 11, line 66, for "aprts" read --parts--.
Column 14, line 42, for "Reference" read --Reference A--.
Column 14, line 49, for "Reference a" read --Reference A--.
Column 16, heading under Table 3, for "Propritary"
     read --Proprietary--.
Column 17, heading under Table 3, for "Propritary"
     read --Proprietary--.
```

Signed and Sealed this

Fourth Day of November 1980

[SEAL]

Attest:

SIDNEY A. DIAMOND

Attesting Officer

Commissioner of Patents and Trademarks